(12) United States Patent
Monsees et al.

(10) Patent No.: US 10,834,964 B2
(45) Date of Patent: *Nov. 17, 2020

(54) METHOD AND SYSTEM FOR VAPORIZATION OF A SUBSTANCE

(71) Applicant: Juul Labs, Inc., San Francisco, CA (US)

(72) Inventors: James Monsees, San Francisco, CA (US); Adam Bowen, San Francisco, CA (US)

(73) Assignee: JUUL LABS, INC., San Francisco, CA (US)

(*) Notice: Subject to any disclaimer, the term of this patent is extended or adjusted under 35 U.S.C. 154(b) by 909 days.

This patent is subject to a terminal disclaimer.

(21) Appl. No.: 14/578,193

(22) Filed: Dec. 19, 2014

(65) Prior Publication Data

US 2015/0150308 A1 Jun. 4, 2015

Related U.S. Application Data

(63) Continuation of application No. 11/485,168, filed on Jul. 11, 2006, now Pat. No. 9,675,109.

(Continued)

(51) Int. Cl.
*A24F 47/00* (2020.01)
*A61M 15/00* (2006.01)
(Continued)

(52) U.S. Cl.
CPC ............. *A24F 47/008* (2013.01); *A24D 1/14* (2013.01); *A24F 13/04* (2013.01); *A24F 47/006* (2013.01);
(Continued)

(58) Field of Classification Search
None
See application file for complete search history.

(56) References Cited

U.S. PATENT DOCUMENTS

| 374,584 A | 12/1887 | Cook |
| 576,653 A | 2/1897 | Bowlby |

(Continued)

FOREIGN PATENT DOCUMENTS

| CA | 2641869 A1 | 5/2010 |
| CN | 85106876 A | 9/1986 |

(Continued)

OTHER PUBLICATIONS

Grotenhermen et al.; Developing science-based per se limits for driving under the influence of cannabis (DUIC): findings and recommendations by an expert panel; retrieved Feb. 9, 2017 from (http://www.canorml.org/healthfacts/DUICreport.2005.pdf); 49 pages; Sep. 2005.

(Continued)

*Primary Examiner* — Phu H Nguyen
(74) *Attorney, Agent, or Firm* — Mintz Levin Cohn Ferris Glovsky and Popeo, P.C.

(57) ABSTRACT

A smoking device for generating and releasing smoking vapor free from contamination into the mouth of a user comprising a mouthpiece for providing vapor for inhalation to a user including a tubular casing containing a heater for heating a smoking substance at a substantially constant low temperature by regulating the flow of fuel by a thermal regulator and further having means for visual indication of the operation of the device.

32 Claims, 3 Drawing Sheets

Related U.S. Application Data

(60) Provisional application No. 60/700,105, filed on Jul. 19, 2005.

(51) Int. Cl.
  *A61M 15/06* (2006.01)
  *A61M 11/04* (2006.01)
  *A24D 1/14* (2006.01)
  *A24F 13/04* (2006.01)

(52) U.S. Cl.
  CPC ......... *A61M 11/042* (2014.02); *A61M 11/048* (2014.02); *A61M 15/0028* (2013.01); *A61M 15/06* (2013.01); *A61M 2205/0266* (2013.01); *A61M 2205/3368* (2013.01)

(56) References Cited

U.S. PATENT DOCUMENTS

| | | |
|---|---|---|
| 595,070 A | 12/1897 | Oldenbusch |
| 720,007 A | 2/1903 | Dexter |
| 799,844 A | 9/1905 | Fuller |
| 968,160 A | 8/1910 | Johnson |
| 969,076 A | 8/1910 | Pender |
| 1,067,531 A | 7/1913 | MacGregor |
| 1,163,183 A | 12/1915 | Stoll |
| 1,299,162 A | 4/1919 | Fisher |
| 1,505,748 A | 8/1924 | Louis |
| 1,552,877 A | 9/1925 | Phillipps et al. |
| 1,632,335 A | 6/1927 | Hiering |
| 1,706,244 A | 3/1929 | Louis |
| 1,845,340 A | 2/1932 | Ritz |
| 1,972,118 A | 9/1934 | McDill |
| 1,998,683 A | 4/1935 | Montgomery |
| 2,031,363 A | 2/1936 | Elof |
| 2,039,559 A | 5/1936 | Segal |
| 2,104,266 A | 1/1938 | McCormick |
| 2,159,698 A | 5/1939 | Harris et al. |
| 2,177,636 A | 10/1939 | Coffelt et al. |
| 2,195,260 A | 3/1940 | Rasener |
| 2,231,909 A | 2/1941 | Hempel |
| 2,327,120 A | 8/1943 | McCoon |
| 2,460,427 A | 2/1949 | Musselman et al. |
| 2,483,304 A | 9/1949 | Rudolf |
| 2,502,561 A | 4/1950 | Ludwig |
| 2,765,949 A | 10/1956 | Swan |
| 2,830,597 A | 4/1958 | Kummli |
| 2,860,638 A | 11/1958 | Bartolomeo |
| 2,897,958 A | 8/1959 | Tarleton et al. |
| 2,935,987 A | 5/1960 | Ackerbauer |
| 3,146,937 A | 9/1964 | Joseph |
| 3,258,015 A | 5/1966 | Ellis et al. |
| 3,271,719 A | 9/1966 | Ovshinsky |
| 3,292,634 A | 12/1966 | Beucler |
| 3,373,915 A | 3/1968 | Anderson et al. |
| 3,420,360 A | 1/1969 | Young |
| 3,443,827 A | 5/1969 | Acker et al. |
| 3,456,645 A | 7/1969 | Brock |
| 3,479,561 A | 11/1969 | Janning |
| 3,567,014 A | 3/1971 | Feigelman |
| 3,675,661 A | 7/1972 | Weaver |
| 3,707,017 A | 12/1972 | Paquette |
| 3,792,704 A | 2/1974 | Parker |
| 3,815,597 A | 6/1974 | Gottelman |
| 3,861,523 A | 1/1975 | Fountain et al. |
| 3,941,300 A | 3/1976 | Troth |
| 4,020,853 A | 5/1977 | Nuttal |
| 4,049,005 A | 9/1977 | Hernandez et al. |
| 4,066,088 A | 1/1978 | Ensor |
| 4,207,976 A | 6/1980 | Herman |
| 4,215,708 A | 8/1980 | Bron |
| 4,219,032 A | 8/1980 | Tabatznik et al. |
| 4,303,083 A | 12/1981 | Burruss |
| 4,506,683 A | 3/1985 | Cantrell et al. |
| 4,519,319 A | 5/1985 | Howlett |
| 4,520,938 A | 6/1985 | Finke |
| 4,595,024 A | 6/1986 | Greene et al. |
| 4,648,393 A | 3/1987 | Landis et al. |
| 4,708,151 A | 11/1987 | Shelar |
| 4,735,217 A | 4/1988 | Gerth et al. |
| 4,771,796 A | 9/1988 | Myer |
| 4,793,365 A | 12/1988 | Sensabaugh, Jr. et al. |
| 4,794,323 A | 12/1988 | Zhou et al. |
| 4,798,310 A | 1/1989 | Kasai et al. |
| 4,813,536 A | 3/1989 | Willis |
| 4,819,665 A | 4/1989 | Roberts et al. |
| 4,830,028 A | 5/1989 | Lawson et al. |
| 4,836,224 A | 6/1989 | Lawson et al. |
| 4,846,199 A | 7/1989 | Rose |
| 4,848,374 A | 7/1989 | Chard et al. |
| 4,848,563 A | 7/1989 | Robbins |
| 4,893,639 A | 1/1990 | White |
| 4,907,606 A | 3/1990 | Lilja et al. |
| 4,941,483 A | 7/1990 | Ridings |
| 4,944,317 A * | 7/1990 | Thal ................. A24D 1/14 131/348 |
| 4,947,874 A | 8/1990 | Brooks et al. |
| 4,947,875 A | 8/1990 | Brooks et al. |
| 5,005,759 A | 4/1991 | Bouche |
| 5,020,548 A | 6/1991 | Farrier et al. |
| 5,027,836 A | 7/1991 | Shannon et al. |
| 5,031,646 A | 7/1991 | Lippiello et al. |
| 5,050,621 A | 9/1991 | Creighton et al. |
| 5,060,671 A * | 10/1991 | Counts ................. A24F 47/008 128/202.21 |
| 5,065,776 A | 11/1991 | Lawson et al. |
| 5,076,297 A | 12/1991 | Farrier et al. |
| 5,105,831 A | 4/1992 | Banerjee et al. |
| 5,105,838 A | 4/1992 | White et al. |
| 5,123,530 A | 6/1992 | Lee |
| 5,133,368 A | 7/1992 | Neumann et al. |
| 5,144,962 A * | 9/1992 | Counts ................. A24F 47/008 128/200.14 |
| 5,152,456 A | 10/1992 | Ross et al. |
| 5,183,062 A | 2/1993 | Clearman et al. |
| 5,224,498 A | 7/1993 | Deevi et al. |
| 5,240,012 A | 8/1993 | Ehrman et al. |
| 5,249,586 A | 10/1993 | Morgan et al. |
| 5,261,424 A | 11/1993 | Sprinkel, Jr. |
| 5,269,237 A | 12/1993 | Baker et al. |
| 5,269,327 A | 12/1993 | Counts et al. |
| 5,303,720 A | 4/1994 | Banerjee et al. |
| 5,322,075 A | 6/1994 | Deevi et al. |
| 5,324,498 A | 6/1994 | Streusand et al. |
| 5,372,148 A | 12/1994 | McCafferty et al. |
| 5,388,574 A | 2/1995 | Ingebrethsen |
| 5,449,078 A | 9/1995 | Akers |
| 5,456,269 A | 10/1995 | Kollasch |
| 5,497,791 A | 3/1996 | Bowen et al. |
| 5,529,078 A | 6/1996 | Rehder et al. |
| 5,579,934 A | 12/1996 | Buono |
| 5,591,368 A | 1/1997 | Fleischhauer et al. |
| 5,605,226 A | 2/1997 | Hernlein |
| 5,641,064 A | 6/1997 | Goserud |
| 5,649,552 A | 7/1997 | Cho et al. |
| 5,666,977 A | 9/1997 | Higgins |
| 5,666,978 A | 9/1997 | Counts et al. |
| 5,708,258 A | 1/1998 | Counts et al. |
| 5,730,118 A | 3/1998 | Hermanson |
| 5,730,158 A | 3/1998 | Collins et al. |
| 5,746,587 A | 5/1998 | Racine et al. |
| 5,810,164 A | 9/1998 | Rennecamp |
| 5,819,756 A | 10/1998 | Mielordt |
| 5,845,649 A | 12/1998 | Saito et al. |
| 5,865,185 A | 2/1999 | Collins et al. |
| 5,881,884 A | 3/1999 | Podosek |
| 5,931,828 A | 8/1999 | Durkee |
| 5,934,289 A | 8/1999 | Watkins et al. |
| 5,938,018 A | 8/1999 | Keaveney et al. |
| 5,944,025 A | 8/1999 | Cook et al. |
| 5,994,025 A | 8/1999 | Cook et al. |
| 5,954,979 A | 9/1999 | Counts et al. |
| 5,967,310 A | 10/1999 | Hill |
| 5,975,415 A | 11/1999 | Zehnal |

(56) References Cited

U.S. PATENT DOCUMENTS

| | | |
|---|---|---|
| 5,979,460 A | 11/1999 | Matsumura |
| 5,996,589 A | 12/1999 | St. Charles |
| 6,053,176 A | 4/2000 | Adams |
| 6,089,857 A | 7/2000 | Matsuura et al. |
| 6,095,153 A | 8/2000 | Kessler et al. |
| 6,102,036 A | 8/2000 | Slutsky et al. |
| 6,125,853 A | 10/2000 | Susa et al. |
| 6,155,268 A | 12/2000 | Takeuchi |
| 6,164,287 A * | 12/2000 | White ............... A24F 47/008 131/194 |
| 6,196,232 B1 | 3/2001 | Chkadua |
| 6,234,169 B1 | 5/2001 | Bulbrook et al. |
| 6,269,966 B1 | 8/2001 | Pallo et al. |
| 6,272,933 B1 * | 8/2001 | Gradon ............ A61M 16/1075 128/203.16 |
| 6,324,261 B1 | 11/2001 | Merte |
| 6,349,728 B1 | 2/2002 | Pham |
| 6,381,739 B1 | 4/2002 | Breternitz, Jr. et al. |
| 6,386,371 B1 | 5/2002 | Parsons |
| 6,431,363 B1 | 8/2002 | Hacker |
| 6,446,793 B1 | 9/2002 | Layshock |
| 6,510,982 B2 | 1/2003 | White et al. |
| 6,532,965 B1 | 3/2003 | Abhulimen et al. |
| 6,536,442 B2 | 3/2003 | St. Charles et al. |
| 6,557,708 B2 | 5/2003 | Polacco |
| 6,598,607 B2 | 7/2003 | Adiga et al. |
| 6,603,924 B2 | 8/2003 | Brown et al. |
| 6,606,998 B1 | 8/2003 | Gold |
| 6,612,404 B2 | 9/2003 | Sweet et al. |
| 6,615,840 B1 | 9/2003 | Fournier et al. |
| 6,622,867 B2 | 9/2003 | Menceles |
| 6,655,379 B2 | 12/2003 | Clark et al. |
| 6,672,762 B1 | 1/2004 | Faircloth et al. |
| 6,688,313 B2 | 2/2004 | Wren et al. |
| 6,726,006 B1 | 4/2004 | Funderburk et al. |
| 6,772,756 B2 * | 8/2004 | Shayan ............... A61M 11/041 128/202.21 |
| 6,799,576 B2 | 10/2004 | Farr |
| 6,803,545 B2 | 10/2004 | Blake et al. |
| 6,805,545 B2 | 10/2004 | Slaboden |
| 6,810,883 B2 | 11/2004 | Felter et al. |
| 6,827,573 B2 | 12/2004 | St. Charles et al. |
| 6,954,979 B2 | 10/2005 | Logan |
| 7,000,775 B2 | 2/2006 | Gelardi et al. |
| 7,015,796 B2 | 3/2006 | Snyder |
| 7,434,584 B2 | 10/2008 | Steinberg |
| 7,488,171 B2 | 2/2009 | St. Charles et al. |
| 7,546,703 B2 | 6/2009 | Johnske et al. |
| 7,644,823 B2 | 1/2010 | Gelardi et al. |
| 7,767,698 B2 | 8/2010 | Warchol et al. |
| 7,801,573 B2 | 9/2010 | Yazdi et al. |
| 7,815,332 B1 | 10/2010 | Smith |
| 7,832,410 B2 | 11/2010 | Hon |
| 8,156,944 B2 | 4/2012 | Hon |
| 8,322,350 B2 | 12/2012 | Lipowicz |
| 8,371,310 B2 | 2/2013 | Brenneise |
| 8,381,739 B2 | 2/2013 | Gonda |
| 8,387,612 B2 | 3/2013 | Damani et al. |
| 8,511,318 B2 | 8/2013 | Hon |
| 8,671,952 B2 | 3/2014 | Winterson et al. |
| 8,741,348 B2 | 6/2014 | Hansson et al. |
| 8,915,254 B2 | 12/2014 | Monsees et al. |
| 8,925,555 B2 | 1/2015 | Monsees et al. |
| 8,991,402 B2 | 3/2015 | Monsees et al. |
| 9,215,895 B2 | 12/2015 | Bowen et al. |
| 2001/0015209 A1 | 8/2001 | Zielke |
| 2001/0032643 A1 | 10/2001 | Hochrainer et al. |
| 2001/0032795 A1 | 10/2001 | Weinstein et al. |
| 2001/0052480 A1 | 12/2001 | Kawaguchi et al. |
| 2002/0029779 A1 * | 3/2002 | Schmidt ............ A61M 15/0086 128/205.25 |
| 2002/0078951 A1 | 6/2002 | Nichols et al. |
| 2002/0175164 A1 | 11/2002 | Dees et al. |
| 2003/0005926 A1 | 1/2003 | Jones et al. |
| 2003/0089377 A1 | 5/2003 | Hajaligol et al. |
| 2003/0150451 A1 | 8/2003 | Shayan |
| 2003/0154991 A1 | 8/2003 | Fournier et al. |
| 2004/0031495 A1 | 2/2004 | Steinberg |
| 2004/0050382 A1 | 3/2004 | Goodchild |
| 2004/0099266 A1 | 5/2004 | Cross et al. |
| 2004/0149296 A1 | 8/2004 | Rostami et al. |
| 2004/0149624 A1 | 8/2004 | Wischusen et al. |
| 2004/0173229 A1 | 9/2004 | Crooks et al. |
| 2004/0182403 A1 | 9/2004 | Andersson et al. |
| 2004/0221857 A1 | 11/2004 | Dominguez |
| 2004/0237974 A1 | 12/2004 | Min |
| 2005/0016549 A1 | 1/2005 | Banerjee et al. |
| 2005/0016550 A1 | 1/2005 | Katase |
| 2005/0034723 A1 | 2/2005 | Bennett et al. |
| 2005/0061759 A1 | 3/2005 | Doucette |
| 2005/0069831 A1 | 3/2005 | St. Charles et al. |
| 2005/0090798 A1 | 4/2005 | Clark et al. |
| 2005/0118545 A1 | 6/2005 | Wong |
| 2005/0145533 A1 | 7/2005 | Seligson |
| 2005/0172976 A1 | 8/2005 | Newman et al. |
| 2005/0244521 A1 | 11/2005 | Strickland et al. |
| 2005/0268911 A1 | 12/2005 | Cross et al. |
| 2006/0018840 A1 | 1/2006 | Lechuga Ballesteros et al. |
| 2006/0054676 A1 | 3/2006 | Wischusen |
| 2006/0102175 A1 | 5/2006 | Nelson |
| 2006/0150991 A1 | 7/2006 | Lee |
| 2006/0191546 A1 | 8/2006 | Takano et al. |
| 2006/0191548 A1 | 8/2006 | Strickland et al. |
| 2006/0196518 A1 | 9/2006 | Hon |
| 2006/0254948 A1 | 11/2006 | Herbert et al. |
| 2006/0255105 A1 | 11/2006 | Sweet |
| 2007/0006889 A1 | 1/2007 | Kobal et al. |
| 2007/0045288 A1 | 3/2007 | Nelson |
| 2007/0062548 A1 | 3/2007 | Horstmann et al. |
| 2007/0074734 A1 | 4/2007 | Braunshteya et al. |
| 2007/0098148 A1 | 5/2007 | Sherman |
| 2007/0102013 A1 | 5/2007 | Adams et al. |
| 2007/0125765 A1 | 6/2007 | Nelson |
| 2007/0144514 A1 | 6/2007 | Yeates et al. |
| 2007/0163610 A1 | 7/2007 | Lindell et al. |
| 2007/0215164 A1 | 9/2007 | Mehio |
| 2007/0235046 A1 | 10/2007 | Gedevanishvili |
| 2007/0267033 A1 | 11/2007 | Mishra et al. |
| 2007/0277816 A1 | 12/2007 | Morrison et al. |
| 2007/0280652 A1 | 12/2007 | Williams |
| 2007/0283972 A1 | 12/2007 | Monsees et al. |
| 2008/0000763 A1 | 1/2008 | Cove |
| 2008/0023003 A1 | 1/2008 | Rosenthal |
| 2008/0029095 A1 | 2/2008 | Esser |
| 2008/0092912 A1 | 4/2008 | Robinson et al. |
| 2008/0149118 A1 | 6/2008 | Oglesby et al. |
| 2008/0216828 A1 | 9/2008 | Wensley et al. |
| 2008/0257367 A1 | 10/2008 | Paterno et al. |
| 2008/0276947 A1 | 11/2008 | Martzel |
| 2009/0004249 A1 | 1/2009 | Gonda |
| 2009/0095287 A1 | 4/2009 | Emarlou |
| 2009/0111287 A1 | 4/2009 | Lindberg et al. |
| 2009/0126745 A1 | 5/2009 | Hon |
| 2009/0133691 A1 | 5/2009 | Yamada et al. |
| 2009/0133703 A1 | 5/2009 | Strickland et al. |
| 2009/0133704 A1 | 5/2009 | Strickland et al. |
| 2009/0151717 A1 | 6/2009 | Bowen |
| 2009/0230117 A1 | 9/2009 | Fernando et al. |
| 2009/0255534 A1 | 10/2009 | Paterno |
| 2009/0260641 A1 | 10/2009 | Monsees |
| 2009/0260642 A1 | 10/2009 | Monsees |
| 2009/0267252 A1 | 10/2009 | Ikeyama |
| 2009/0268668 A1 | 10/2009 | Tinnakornsrisuphap et al. |
| 2009/0272379 A1 | 11/2009 | Thorens |
| 2009/0293892 A1 * | 12/2009 | Williams ............ A24F 47/008 131/328 |
| 2009/0293895 A1 | 12/2009 | Axelsson et al. |
| 2010/0006092 A1 | 1/2010 | Hale |
| 2010/0031968 A1 | 2/2010 | Sheikh |
| 2010/0156193 A1 | 6/2010 | Rhodes et al. |
| 2010/0163063 A1 | 7/2010 | Fernando et al. |
| 2010/0186757 A1 | 7/2010 | Crooks et al. |
| 2010/0275938 A1 | 11/2010 | Roth et al. |
| 2011/0030706 A1 | 2/2011 | Gibson et al. |

(56) References Cited

U.S. PATENT DOCUMENTS

| | | |
|---|---|---|
| 2011/0036346 A1 | 2/2011 | Cohen et al. |
| 2011/0094523 A1 | 4/2011 | Thorens et al. |
| 2011/0108023 A1 | 5/2011 | McKinney |
| 2011/0226236 A1 | 9/2011 | Buchberger |
| 2011/0226266 A1 | 9/2011 | Tao |
| 2011/0236002 A1 | 9/2011 | Oglesby et al. |
| 2012/0247494 A1 | 10/2012 | Oglesby et al. |
| 2012/0260927 A1 | 10/2012 | Liu |
| 2012/0325227 A1 | 12/2012 | Robinson et al. |
| 2013/0042865 A1 | 2/2013 | Monsees |
| 2013/0068239 A1 | 3/2013 | Youn |
| 2013/0152922 A1 | 6/2013 | Benassayag et al. |
| 2013/0312742 A1 | 11/2013 | Monsees |
| 2014/0041655 A1 | 2/2014 | Barron |
| 2014/0060552 A1 | 3/2014 | Cohen et al. |
| 2014/0345631 A1 | 11/2014 | Bowen et al. |
| 2014/0366898 A1 | 12/2014 | Monsees |
| 2014/0378790 A1 | 12/2014 | Cohen |
| 2015/0157056 A1 | 6/2015 | Bowen et al. |
| 2015/0208729 A1 | 7/2015 | Monsees et al. |
| 2016/0044967 A1 | 2/2016 | Bowen et al. |
| 2016/0044968 A1 | 2/2016 | Bowen et al. |
| 2016/0174611 A1 | 6/2016 | Monsees et al. |

FOREIGN PATENT DOCUMENTS

| | | |
|---|---|---|
| CN | 1122213 A | 5/1996 |
| CN | 1333657 A | 1/2002 |
| CN | 1633247 A | 6/2005 |
| CN | 301472873 S | 2/2011 |
| CN | 302002622 S | 7/2012 |
| CN | 302292447 S | 1/2013 |
| CN | 302311408 S | 1/2013 |
| DE | 4200639 | 7/1992 |
| DE | 19854005 A1 | 5/2000 |
| DE | 19854012 A1 | 5/2000 |
| EP | 0295122 A2 | 12/1988 |
| EP | 0311581 A1 | 4/1989 |
| EP | 0430559 A2 | 6/1991 |
| EP | 0503767 A1 | 9/1992 |
| EP | 0532194 A1 | 3/1993 |
| EP | 0535695 | 4/1993 |
| EP | 0283672 B1 | 9/1993 |
| EP | 1458388 A | 9/2004 |
| EP | 2772148 | 9/2014 |
| EP | 2319934 B1 | 9/2015 |
| ES | 2118034 A1 | 9/1998 |
| GB | 1025630 A | 4/1966 |
| GB | 1065678 | 4/1967 |
| IE | S2005-0051 | 2/2005 |
| IE | S2005-0563 | 8/2005 |
| IE | S2005-0615 | 9/2005 |
| JP | 61-108364 | 5/1986 |
| JP | 62-278975 | 12/1987 |
| JP | 64-37276 A | 2/1989 |
| JP | 2-124082 | 5/1990 |
| JP | 02-145179 A | 6/1990 |
| JP | 03-049671 | 4/1991 |
| JP | H03180166 A | 8/1991 |
| JP | 05-115272 | 5/1993 |
| JP | 1993-115272 | 5/1993 |
| JP | 09-075058 | 3/1997 |
| JP | 10-501999 A | 2/1998 |
| JP | 11-178563 | 6/1999 |
| JP | 2000-203639 | 7/2000 |
| JP | 2000-236865 | 9/2000 |
| JP | 2001-165437 A | 6/2001 |
| JP | 1991-232481 | 10/2001 |
| JP | 2002-529111 | 9/2002 |
| JP | 2005-034021 A | 2/2005 |
| JP | 2005-506080 | 3/2005 |
| JP | 2006504430 A | 2/2006 |
| KR | 10-0193885 B1 | 6/1999 |
| WO | WO 95/01137 A1 | 1/1995 |
| WO | WO97/12639 A1 | 4/1997 |
| WO | WO-9963844 A1 | 12/1999 |
| WO | WO-2000/28842 A1 | 5/2000 |
| WO | WO-2001/82725 A1 | 11/2001 |
| WO | WO-2003/056948 A1 | 7/2003 |
| WO | WO 2003/070031 A1 | 8/2003 |
| WO | WO-03082031 A1 | 10/2003 |
| WO | WO03/094900 A1 | 11/2003 |
| WO | WO 03/103387 A2 | 12/2003 |
| WO | WO-2004041006 A1 | 5/2004 |
| WO | WO 2004/064548 A1 | 8/2004 |
| WO | WO2004/080216 A1 | 9/2004 |
| WO | WO-2005/020726 A1 | 3/2005 |
| WO | WO-2006/015070 | 2/2006 |
| WO | WO-2006/082571 A1 | 8/2006 |
| WO | WO-2007/012007 A2 | 1/2007 |
| WO | WO-2007/026131 | 3/2007 |
| WO | WO-2007/039794 A2 | 4/2007 |
| WO | WO-2007/042941 | 4/2007 |
| WO | WO2007/078273 A1 | 7/2007 |
| WO | WO-2009/079641 A2 | 6/2009 |
| WO | WO-2009/079641 A3 | 6/2009 |
| WO | WO 2013/025921 A1 | 2/2013 |
| WO | WO-2014/201432 | 12/2014 |
| WO | WO2015/084544 A1 | 6/2015 |
| WO | WO2015/175979 A1 | 11/2015 |

OTHER PUBLICATIONS

Monsees et al.; U.S. Appl. No. 15/368,539 entitled "Low temperature electronic vaporization device and methods," filed Dec. 2, 2016.

Bowen et al.; U.S. Appl. No. 15/309,554 entitled "Systems and methods for aerosolizing a smokeable material," filed Nov. 8, 2016.

Monsees et al.; U.S. Appl. No. 15/379,898 entitled "Vaporization device systems and methods," filed Dec. 15, 2016.

Hatton et al.; U.S. Appl. No. 15/396,584 entitled "Leak-resistant vaporizer cartridges for use with cannabinoids," filed Dec. 31, 2016.

Burch et al.; Effect of pH on nicotine absorption and side effects produced by aerosolized nicotine; Journal of Aerosol Medicine: Deposition, Clearance, and Effects in the Lung; 6(1); pp. 45-52; 1993.

Food & Drug Administration; Warning letter to The Compounding Pharmacy; retrieved Oct. 10, 2014 from http://www.fda.gov/ICECI/EnfocementActions/WarningLetters/2002/ucm144843.htm; 3 pgs.; Apr. 9, 2002.

Harvest Vapor; American Blend Tobacco (product info.); retrieved from the internet (http://harvestvapor.com/); 2 pgs.; print/retrieval date: Oct. 10, 2014.

Inchem; Benzoic Acid; JECFA Evaluation Summary; retrieved Oct. 10, 2014 from http://www.inchem.org/documents/jecfa/feceval/jec_184.htm; 2 pgs..; May 28, 2005.

Inchem; Levulinic Acid; JECFA Evaluation Summary; retrieved Oct. 10, 2014 from http://www.inchem.org/documents/jecfa/feceval/jec_1266.htm; 1 pg.; Mar. 10, 2003.

Inchem; Pyruvic Acid; JECFA Evaluation Summary; retrieved Oct. 10, 2014 from http://www.inchem.org/documents/jecfa/feceval/jec_2072.htm; 1 pg.; Jan. 29, 2003.

Inchem; Sorbic Acid; JECFA Evaluation Summary; retrieved Oct. 10, 2014 from http://www.inchem.org/documents/jecfa/feceval/jec_2181.htm; 1 pg.; May 29, 2005.

Perfetti; Structural study of nicotine salts; Beitrage zur Tabakforschung International; Contributions to Tobacco Research; 12(2); pp. 43-54; Jun. 1983.

Seeman et al.; The form of nicotine in tobacco. Thermal transfer of nicotine and nicotine acid salts to nicotine in the gas phase; J Aric Food Chem.; 47(12); pp. 5133-5145; Dec. 1999.

Monsees et al.; U.S. Appl. No. 15/257,748 entitled "Cartridge for use with a vaporizer device," filed Sep. 6, 2016.

Monsees et al.; U.S. Appl. No. 15/257,760 entitled "Vaporizer apparatus," filed Sep. 6, 2016.

Monsees et al.; U.S. Appl. No. 15/257,768 entitled "Vaporizer apparatus," filed Sep. 6, 2016.

Monsees et al.; U.S. Appl. No. 15/261,823 entitled "Low temperature electronic vaporization device and methods," filed Sep. 9, 2016.

(56) References Cited

OTHER PUBLICATIONS

European Patent Application No. 12824116.3 Extended European Search Report dated Mar. 4, 2015.
AU Patent Application No. 2013205041 Patent Examination Report No. 2 dated Jul. 21, 2015.
EP 14153324.0 Communication dated May 18, 2015.
EP14200318.5 Extended European Search Report dated May 18, 2015.
European Patent Application No. 14153325.7 Office Action dated Feb. 23, 2015.
Japanese Patent Application No. 2010-539818 Decision of Refusal dated Mar. 31, 2015.
Korean Patent Application No. 10-2015-7000063 Office Action dated May 1, 2015.
Korean Patent Publication No. 10-0193885 (Jun. 1, 1999).
Russian Patent Application No. 2014109394 Office Action dated Feb. 26, 2015.
U.S. Appl. No. 13/837,438 Office Action dated Jul. 31, 2015.
Monsees, J.; U.S. Appl. No. 12/115,400 entitled "Method and System for Vaporization of a Substance", filed May 5, 2008.
Bowen et al.; U.S. Appl. No. 14/960,259 entitled "Calibrated Dose Control", filed Dec. 4, 2015.
Monsees et al.; U.S. Appl. No. 15/165,954 entitled "Devices for vaporization of a substance," filed May 26, 2016.
Monsees et al.; U.S. Appl. No. 15/166,001 entitled "Electronic vaporization device," filed May 26, 2016.
Monsees et al.; U.S. Appl. No. 15/165,972 entitled "Portable devices for generating an inhalable vapor," filed May 26, 2016.
Bowen et al.; U.S. Appl. No. 15/101,303 entitled "Nicotine liquid formulations for aerosol devices and methods thereof," filed Jun. 2, 2016.
"Lighter." Merriam-Webster Online Dictionary. 2009. Merriam-Webster Online. Jun. 8, 2009 [http://www.merriam-webster.com/dictionary/lighter].
Baker et al., "The pyrolysis of tobacco ingredients," J. Anal. Appl. Pyrolysis, vol. 71, pp. 223-311 (2004).
Bombick, et al. Chemical and biological studies of a new cigarette that primarily heats tobacco. Part 2. In vitro toxicology of mainstream smoke condensate. Food and Chemical Toxicology. 1997; 36:183-190.
Bombick, et al. Chemical and biological studies of a new cigarette that primarily heats tobacco. Part 3. In vitro toxicity of whole smoke. Food and Chemical Toxicology. 1998; 36:191-197.
Borgerding, et al. Chemical and biological studies of a new cigarette that primarily heats tobacco. Part 1. Chemical composition of mainstream smoke. Food and Chemical Toxicology. 1997; 36:169-182.
Davis & Nielsen, "Marketing, Processing and Storage: Green Leaf Threshing and Redrying Tobacco," Tobacco Production, Chemistry and Technology, (1999) Section 10B, pp. 330-333, Bill Ward, Expert Leaf Tobacco Company, Wilson, North Carolina, USA.
European Application No. 14153340.6 Search report and search opinion dated Oct. 8, 2014.
European Application No. 06787864.5 Extended European Search Report dated Mar. 22, 2013.
European Application No. 08860921.9 Extended Search Report dated Oct. 10, 2013.
European Application No. 14153321.6 Office action dated May 22, 2014.
European Application No. 14153323.2 Office action dated May 22, 2014.
European Application No. 14153324.0 Office action dated May 22, 2014.
European Application No. 14153327.3 Search report dated May 26, 2014.
European Application No. 14153326.5 Office action dated May 27, 2014.
European Application No. 14153323.2 Communication dated Jan. 29, 2015.
European Application No. 14153326.5 Communication dated Jan. 29, 2015.
European Application No. 14153321.6 Communication dated Jan. 28, 2015.
European Application No. 14153327.3 Communication dated Jan. 30, 2015.
European Application No. 13189967.6 Search Report dated Jun. 13, 2014.
European Application No. 14153325.7 Search report dated Jun. 20, 2014.
European Application No. 14153327.3 Office action dated Jun. 27, 2014.
European Application No. 06787864.5 Exam Report dated Nov. 12, 2013.
European Application No. 14153324.0 Search report dated May 9, 2014.
European Application No. 14153326.5 Search Report dated May 9, 2014.
European Application No. 14153321.6 Search report dated May 9, 2014.
European Application No. 14153323.2 Search report dated May 9, 2014.
Ingebrethsen et al., "Electronic Cigarette aerosol particle size distribution measurements", Inhalation Toxicology, 2012; 24 (14): 976-984.
Kuo et al. Applications of Turbulent and Multiphase Combustion, Appendix D: Particle Size—U.S. Sieve Size and Tyler Screen Mesh Equivalents, 2012, p. 541-543.
McCann et al., "Detection of carcinogens as mutagens in the Salmonella/microsome test: Assay of 300 chemicals: discussion." Proct. Nat. Acad. Sci, USA, Mar. 1976, vol. 73 (3), 950-954.
Nicoli et al., Mammalian tumor xenografts induce neovascularization in Zebrafish embryos. Cancer Research, 67:2927-2931 (2007).
PCT/IB2006/002040 International Preliminary Report on Patentability dated Apr. 1, 2008.
PCT/IB2006/002040 International Search Report and Written Opinion dated Mar. 26, 2007.
PCT/IB2006/003842 International Preliminary Report on Patentability dated Apr. 1, 2008.
PCT/IB2006/003842 International Search Report and Written Opinion dated May 31, 2007.
PCT/US06/28039 Corrected Written Opinion dated Dec. 20, 2007.
PCT/US06/28039 International Search Report dated Sep. 6, 2007.
PCT/US06/28039 IPER and Written Opinion dated Jul. 15, 2008.
PCT/US08/87488 IPRP and Written Opinion dated Jun. 22, 2010.
PCT/US2008/87488 International Search Report dated Jul. 13, 2009.
PCT/US2008/87488 Written Opinion dated Jul. 13, 2009.
PCT/US2012/051165 International Preliminary Report on Patentability dated Feb. 18, 2014.
PCT/US2012/051165 International Search Report and Written Opinion dated Oct. 25, 2012.
PCT/US2014/042425 International Search Report and Written Opinion dated Nov. 3, 2014.
Torikai et al., "Effects of temperature, atmosphere and pH on the generation of smoke compounds during tobacco pyrolysis," Food and Chemical Toxicology 42 (2004) 1409-1417.
U.S. Appl. No. 11/485,168 Office Action dated Feb. 4, 2010.
U.S. Appl. No. 11/485,168 Office action dated Mar. 27, 2014.
U.S. Appl. No. 11/485,168 Office Action dated Jun. 23, 2009.
U.S. Appl. No. 11/485,168 Office action dated Jul. 9, 2014.
U.S. Appl. No. 11/485,168 Office Action dated Aug. 3, 2010.
U.S. Appl. No. 11/485,168 Office action dated Sep. 5, 2013.
U.S. Appl. No. 11/485,168 Office Action dated Nov. 3, 2009.
U.S. Appl. No. 11/485,168 Office action dated Dec. 21, 2012.
U.S. Appl. No. 12/336,439 Final Action dated Nov. 25, 2013.
U.S. Appl. No. 12/336,439 Final Office Action dated Feb. 1, 2012.
U.S. Appl. No. 12/336,439 Office action dated Aug. 6, 2014.
U.S. Appl. No. 12/336,439 Office Action dated Aug. 17, 2011.
U.S. Appl. No. 12/336,439 Office Action dated Feb. 22, 2013.
U.S. Appl. No. 12/336,439 Office Action dated Feb. 28, 2014.
U.S. Appl. No. 12/482,379 Final Office Action dated Sep. 5, 2012.

(56) References Cited

OTHER PUBLICATIONS

U.S. Appl. No. 12/482,379 Non Final Office Action dated Dec. 17, 2013.
U.S. Appl. No. 12/482,379 Office Action dated Dec. 22, 2011.
U.S. Appl. No. 13/587,416 Office Action dated Feb. 2, 2015.
U.S. Appl. No. 13/587,416 Office Action dated Oct. 31, 2014.
U.S. Appl. No. 29/446,987 Office Action dated Nov. 13, 2014.
Wells. "Glycerin as a Constituent of Cosmetics and Toilet Preparations." Journal of the Society of Cosmetic Chemists, 1958; 9(1): 19-25.

* cited by examiner

METHOD AND SYSTEM FOR VAPORIZATION OF A SUBSTANCE

CROSS-REFERENCE TO RELATED APPLICATIONS

This application is a continuation application of U.S. application Ser. No. 11/485,168, filed Jul. 11, 2006, which claims the benefit of U.S. Provisional Application No. 60/700,105, filed Jul. 19, 2005, each of which are incorporated herein by reference in their entirety.

BACKGROUND OF THE INVENTION

1. Field of the Invention

The present invention is directed to improvements in smoking devices, particularly to smoking articles which employ a formed tobacco cartridge as a source of producing vapor by heat transfer to the cartridge by conduction, convection, and radiation for smoke and flavor. The present invention relates to self-contained vaporization devices, and more particularly, to a low-temperature vaporization device for use of tobacco product. The device is of an elongated main body with a mouthpiece at one end and an attached tubular casing at the other end having a vaporization chamber and a heater. The mouthpiece and the casing form an unitary unit.

2. Description of the Related Art

Smoking devices, such as cigarette holders and pipes are well known in the art for providing flavored vapor from a smokable substance to a user for therapeutic and smoking pleasure. However, existing devices used have no control of heating and combustion of the tobacco products. The devices tend to produce toxic, tarry and carcinogenic by-products which are harmful and also impart a bitter and burnt taste to a mouth of a user.

A further problem is that there is no control of contamination of the inhaled vapor mixture with heater exhaust gases, due to inappropriate proportioning and location of the inlets and the exhaust vents. Typically, the exhaust gas is used to directly heat the tobacco, and those gases contain harmful byproducts of incomplete combustion.

In an effort to overcome these deficiencies, there have been numerous attempts to provide a device structure and the substance for producing vapor for smoking which is free from harmful by-product and would provide a cool and soothing vapor for smoking.

For example, U.S. Patent Application No. 2004/0237974 A1, published on Dec. 2, 2004 for Min discloses a filtering cigarette and cigar holder which removes tar and nicotine from the tobacco smoke.

U.S. Patent Application No. 2004/0031495 A1, published on Feb. 19, 2004 for Steinberg discloses a vaporization pipe with flame filter which uses a flame to vaporize the smoking substance.

U.S. Pat. No. 6,164,287, issued Dec. 26, 2000 to White, describes a smoking device which produces smoke from tobacco at low temperatures, without producing harmful byproducts.

U.S. Pat. No. 4,848,374, issued Jul. 18, 1989 to Chard et al describe a smoking device to vaporize aerosol precursor, an event which precedes condensation to mainstream aerosol precursor by contact with heated surface rather than by hot gases into the mouth of a smoker.

U.S. Pat. No. 4,219,032, issued Aug. 26, 1980 to Tabatznik et al describe a smoking device wherein an extracted smoke is cooled by passing it through a suitable liquid to provide a soothing smoke.

U.S. Pat. No. 4,020,853, issued May 3, 1977 to Nuttall, describes a smoking pipe made of ceramic material such as colored and ornamental porcelain for enhancing the artistic look, and also to provide a circulating air to keep the outer wall of the pipe cool and safe for handling.

U.S. Pat. No. 3,792,704, issued Feb. 19, 1974 to Parker, describes a pipe tobacco smoking system, wherein the pipe and the tobacco capsule are mutually designed to yield a slim-line smoking combination that can be manufactured from relatively low temperature thermo-plastic material.

SUMMARY OF THE INVENTION

The present invention is drawn to a novel smoking device consisting of a mouthpiece and a casing having a heater, a low temperature vaporization chamber, a fuel tank, an igniter with control means for maintaining equilibrium point by keeping the operating temperature below 400 F, preferably below 350 F during combustion whereby in order to maintain a stable operating temperature, a thermal regulator is used to control flow rate of the fuel.

Accordingly, it is principal object of the invention to provide a mouthpiece made of a high temperature food-safe material, such as ceramic, glass, or high temperature plastics known as PEI resin (brand name Ultem) However, suitable plastic or wood, etc., could also be used but would additionally require an insulating material that would prevent excessive heat reaching the user's lips.

Additionally, air inlets are directed downwards, so that fresh ambient air drawn through mixes with the vapor generated into the vaporization chamber located above the smokable substance cartridge, which is extracted from the cartridge by inlets located below the cartridge and drawn into user's mouth for inhalation.

It is another object of the invention to provide air inlet or inlets having a diameter and direction sized to admit ambient air into the chamber to heat up the substance and not effect the operating temperature and also regulating the velocity of ambient air entering and mixing with the vapor generated from combustion, radiation and convection in the chamber at such a rate that the proportionate inhalation passage provides a perception to the user as if the smoke is drawn through a cigarette.

It is still another object of the invention to provide a heater which is separated from the vapor chamber by an insulating medium such as ring made of PTFE, ceramic or other insulating material and thereby preventing the exhaust gases produced by the heater from entering and contaminating the vapor in the vaporization chamber collected for inhalation.

Another object of the invention to provide a heater is formed of a conductive shell and a catalyst, the shell may be of one or more material formed by welding or pressing together. Whereas, the catalyst could be of platinum or palladium impregnated metal or glass or other suitable material, which provides for efficient flameless combustion of the fuel and glows red when heated to indicate that the device is activated. Additionally, a feedback loop could be employed to regulate the desired temperature.

Preferably the tobacco cartridge formed and shaped for easier insertion into the heating chamber and to snugly fit into the cavity of the heating chamber for improved thermal conduction and vaporization. The cartridges are formed and wrapped into wrapper which does not produce significant amount of harmful gases.

These and other objects of the present invention will become readily apparent upon further review of the following specifications and drawings.

DETAILED DESCRIPTION OF THE INVENTION

Figure 1:
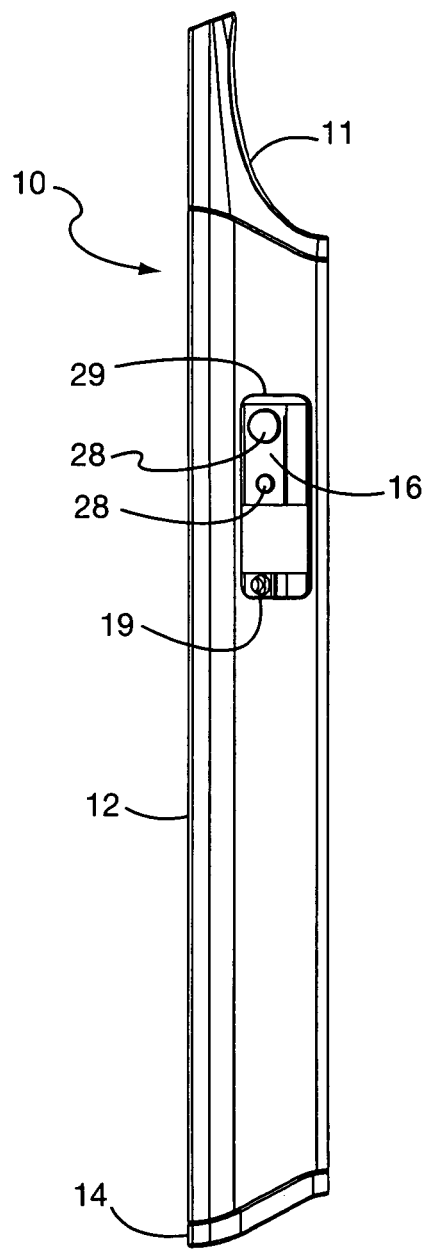
FIG. 1 is a side view of a portable vaporization device, according to a preferred embodiment of the present invention.
Figure 2:
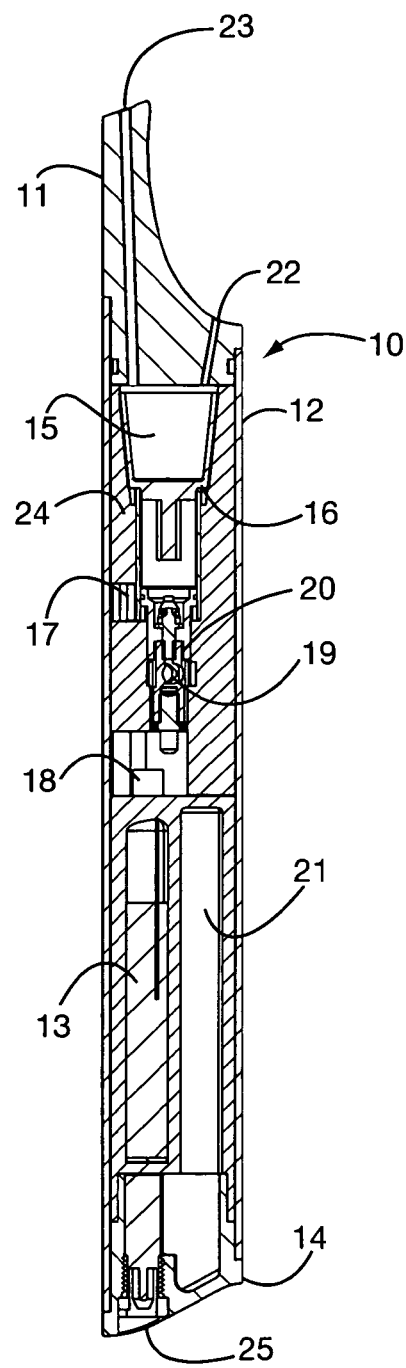
FIG. 2 is a sectional view of the same embodiment.

Referring to FIG. 1 and FIG. 2, the exterior of the device 10 comprises a mouthpiece 11, a tubular case 12, and the base 14 of a butane tank 21. The mouthpiece is removable and creates an airtight seal with the interior of the case. With the mouthpiece removed, a tobacco cartridge (FIG. 5) is introduced to vaporization chamber 15 of a heater 16. The mouthpiece is then reinserted to close the device.

The mouthpiece is made of a high-temperature and food-safe material such as ceramic, glass, or various high-temperature plastics such as PEI resin (brand name Ultem). Design is simplified by use of high temperature materials, but standard plastics or wood, etc, could also be used with the addition of an insulating component that prevents any excessive heat from reaching the user's lips.

To activate the device, the butane tank is pulled axially outward, partially removing it from the case. This starts the flow of butane by opening a master valve 18, and then activating a piezoelectric igniter 13. The tank remains in the partially removed position for the duration of use. While the master valve is open, butane flows through a thermal regulator 17, and into the carburetor 20. Ambient air enters the case through slot 19. A venturi in the carburetor entrains air, causing it to mix with the butane. The mixture then flows into the heater 16.

The lead of the igniter is positioned in the heater. With the spark of the igniter (immediately following the start of gas flow) the gas ignites and heat starts conducting throughout the heater. Heat transfers to the cartridge by conduction, convection, and radiation. The cartridge is shaped to fill the chamber, so as to maximize surface contact for thermal conduction.

As the cartridge heats, vapor generates within the cartridge and in the space immediately above it. When a user draws on the device, fresh air enters through air inlet 22, mixes with the vapor, and the mixture is delivered to the user via the inhalation passage 23. In the preferred embodiment, the air inlet or inlets are directed downward, so as to improve the extraction of vapor from the cartridge. They could also be directed along a diagonal through the mouthpiece, or laterally through the case itself, above the cartridge.

Figure 3:
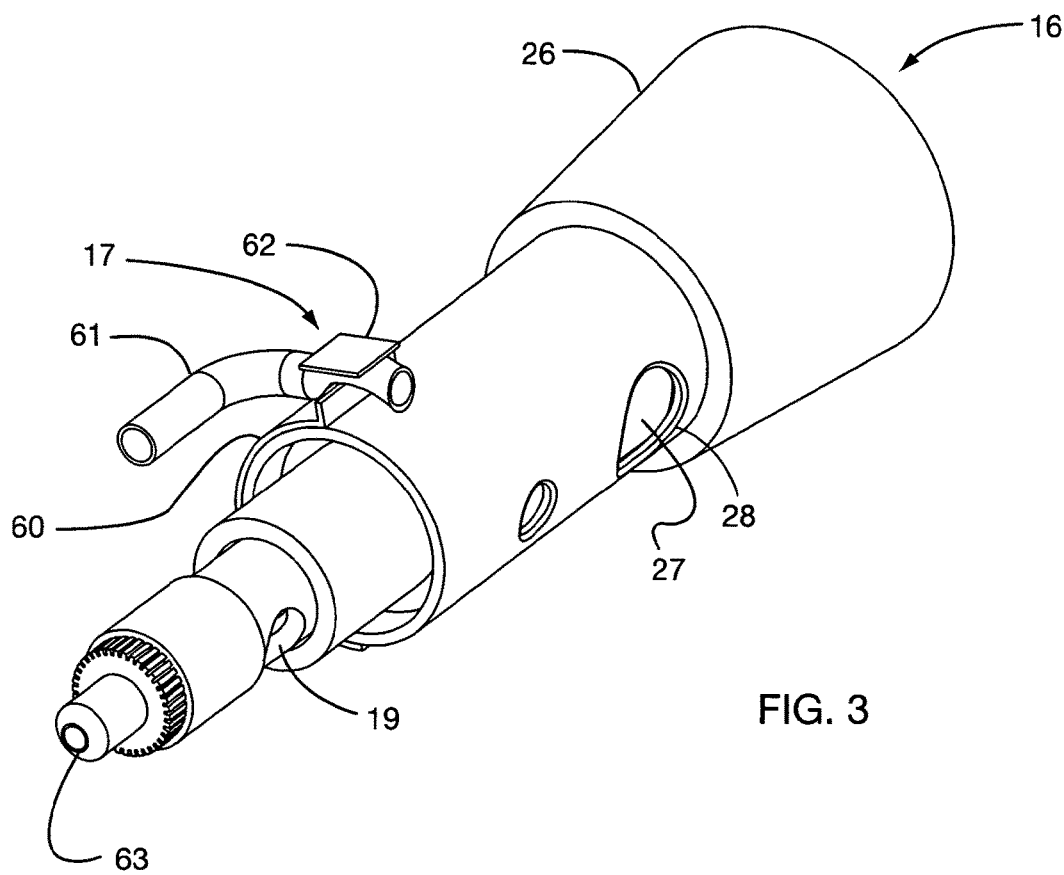
FIG. 3 is a perspective view of a heater, according to the same embodiment.

FIG. 3 depicts a detailed view of the heater 16. The heater comprises a thermally conductive shell 26 and catalyst 27. The shell could be comprised of one material, or a combination of materials welded or pressed together. The catalyst could be platinum- or palladium-impregnated metal or glass, or other suitable material known to those skilled in the art. The catalyst provides for efficient flame-less combustion of the butane. The vent 28 of the heater is positioned such that it is visible through the slot 29 of the body as shown in FIG. 1. This allows the user to see the catalyst which, when heated, can glow red to indicate that the device has been activated.

Referring again to FIG. 3, adjacent to the heater and in intimate thermal contact is the thermal regulator 17. As the temperature of the heater increases, so does that of the regulator. The regulator is designed to restrict the flow of butane as the temperature increases, thus creating a feedback loop. In the preferred embodiment, the regulator consists of a bimetallic strip 60 and silicone tubing 61 which is the conduit of the butane. The two are arranged such that as the bimetallic strip heats up, it curls to pinch the silicone tube and thereby restrict the flow of butane. The reduced flow of butane results in less heat generated. The heater subsequently cools down, and so does the regulator, allowing more butane to flow again. The overall result is that a stable operating temperature is established in the heater. Such a system can be readily tuned to achieve an operating temperature that varies by less than +/−5 degrees Fahrenheit.

The regulator further comprises a moveable backplate 62 which allows adjustability of the operating temperature by adjusting the temperature at which the bi-metallic actuator closes the tube valve. This is to be performed once at manufacture, to calibrate the device. In alternate embodiments, a control means could be used to allow the target temperature of the device changed during operation.

In the preferred embodiment, the regulator comprises in part a bi-metallic strip and silicone tubing valve. In alternate embodiments, the regulator could be comprised of other materials and configurations, as described later.

For the purposes of vaporizing most botanicals in this device, the desired operating temperature is below 400 F; preferably below 350 F.

In the preferred embodiment, the air inlet diameter is sized such that inhalation is somewhat inhibited. This allows time for ambient air entering the chamber to heat up and not affect operating temperature considerably. It also increases velocity of the entering air, which improves circulation and mixing in the vaporization chamber. It also creates a partial vacuum, lowering the vapor point temperature for material contained in the vaporization chamber. The reduction in draw rate can also serve to give the impression of drawing on a cigarette or pipe. Both the fresh air inlet and inhalation passage can be adjusted to provide appropriate draw rate for the operating temperature of the device, and the perception intended for the user.

Once the cartridge is consumed, the device is turned off by pushing the tank back into the case, closing the master valve. The spent tobacco cartridge is removed by opening the device and turning the body over. In the preferred embodiment, the cartridge simply falls out. In alternate embodiments, a mechanism could be used to quickly and easily remove the cartridge. This mechanism could include, but does not require, the use of a pin or slide part to eject the cartridge as another part of the device is moved or removed. The removal mechanism could also involve introduction of a foreign object.

In an alternate embodiment, the mouthpiece is permanently attached to the body. In that case, the vaporization chamber could be accessed by operating a sliding or hinged door, or similar means, built into the device.

The heater of the device is fitted into the case with an insulator 24. The insulator could be made of PEI (brand name Ultem), ceramic, or other insulating material. The insulator serves to minimize thermal transfer from the heater to the case, while creating an air-tight seal. The seal prevents exhaust gases produced by the heater from entering the vaporization chamber. Exhaust gases are instead vented out the case slots. Since the air inlet is distant from the slots, there is substantially no contamination of the inhaled vapor mixture by heater exhaust gases.

In an alternate embodiment, the insulator could be a partially hollow shell, containing a sealed vacuum. In another embodiment, the heater might be sealed directly to the case by braising in a vacuum furnace, so as to create a vacuum between the two and obviate need for an insulator component.

In the preferred embodiment, the tank is made of a translucent material. This allows the user to determine the level of fuel remaining by looking at the base of the tank.

In the preferred embodiment, the case is made of a material that is either a good thermal conductor (such as aluminum), or a poor one (such as ceramics). In both cases, the effect is that the body remains cool enough to touch over a large portion of its surface.

In the preferred embodiment, a bimetallic actuator is used in the regulator. In alternate embodiments, a shape memory alloy actuator such nickel-titanium alloys ("Nitinol") could be used. Alternatively, a paraffin-filled component that expands and contracts to modulate butane flow could be employed. Alternatively, a system could be employed to measure the current temperature, e.g., with a thermocouple sensor and compare it to a prescribed temperature, e.g., with a micro-controller, and by controlling an electromechanical valve, e.g., servo or solenoid valve. In an embodiment with user-selected temperature, as described above, the selected temperature could be used as an input to this system.

In the preferred embodiment, a thermal regulator is used. In an alternate embodiment, the device is constructed without an active regulating element. This could result in reduced complexity and in lowering the overall cost of the device. In this case, the flow of butane is set at a low level. In use, the temperature inside the chamber increases until an equilibrium point where additional heat introduced equals the heat lost to the environment. Heat is lost by conduction through the body of the device, and with the vapor delivered to the user. This equilibrium point determines the operating temperature of the device. By changing the butane flow rate, size and material of the burner, and other factors, the system can be calibrated to provide a fairly stable desired operating temperature.

The principal advantage of the preferred bimetallic regulator feedback loop methods over the equilibrium method is that the operating temperature is not dependent on environmental factors such as ambient temperature and wind.

In the preferred embodiment, a piezo-electric igniter is used. Other igniters could be used, such as, a flint starter or battery-powered resistive coil.

In the preferred embodiment, the butane tank is meant to be refillable, and has a port 25 for that purpose. As an alternate embodiment, the tank might be disposable once its fuel is exhausted. A release mechanism such as a pin or cam would be employed allowing the user to quickly remove the depleted tank and replace it with a full one. The replaceable tank might include additional parts of the device including, but not limited to, the igniter and heater. Butane is the preferred fuel source, but could be replaced by other liquid fuels, such as ethanol.

In alternate embodiments of the present invention, various means of feedback could be used to indicate the following states or metrics of the device: 1) the device is on, 2) the current temperature of the vaporization chamber, 3) the chamber is below a prescribed operating temperature, 4) the chamber has reached a prescribed operating temperature and vapor is ready for consumption, and 5) the chamber has exceeded a prescribed operating temperature.

The means of the feedback includes both physical and electronic implementations. Possibilities include thermochromatic paint, light-emitting diodes and liquid crystal display. The sensing and control means for electronic feedback could be implemented by use of thermocouple and micro-controller, as is known to those skilled in the art.

Active elements contained in botanicals vaporize at different temperatures. In the preferred embodiment, the device is calibrated to establish a single stable temperature, intended for vaporizing solely tobacco or solely chamomile, for example. In alternate embodiments, a control means would be used to select a variety of temperature settings. The user would choose which setting based on the type of cartridge used. The control means could effect a desired temperature mechanically, such as by changing flow rate of the valve, or electronically, such as by electromechanical valve and micro-controller intermediary.

Butane was found to be the most energy-dense and practical fuel source. In alternate embodiments of the invention, the butane heating system is replaced by a battery-powered electric heater or other compact heat source.

Figure 4:
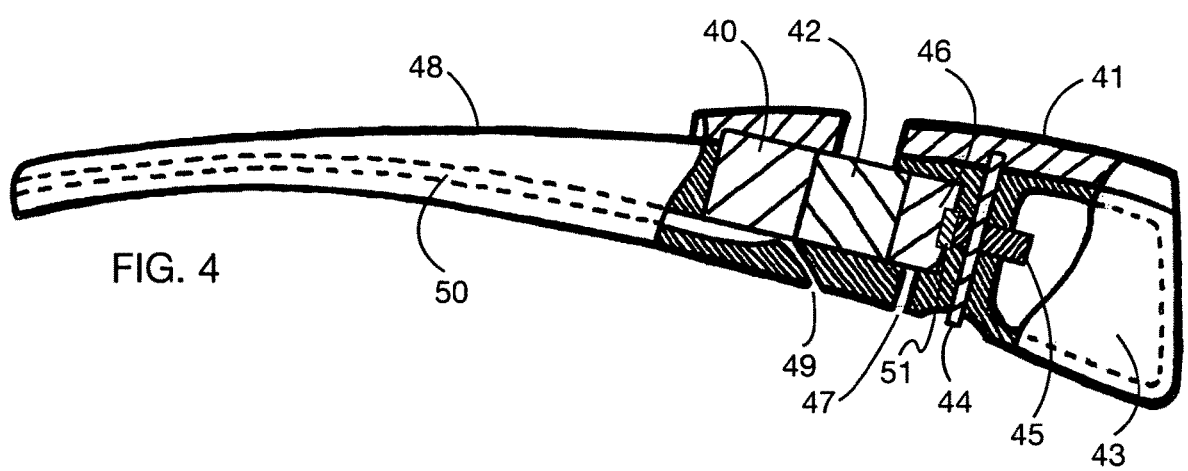
FIG. 4 is a cutaway view of an alternate embodiment according to the present invention.

FIG. 4 depicts a cutaway view of an alternate embodiment which more closely resembles a traditional pipe form. In this embodiment the device retains all of the critical elements from the preferred embodiment. The user inserts a tobacco cartridge 40, under a sliding top piece 41, where the cartridge mates with the heater 42. Fuel held in the tank 43 is released by turning dial 44 to open master valve 45. The fuel travels through the regulator 51, and then through the carburetor 46 where it draws in air through the intake port 47 and catalyzes in a manner similar to that of the preferred embodiment. As the cartridge 40 reaches its operating temperature the user places the mouthpiece 48 in their mouth and draws air in through the inhalation intake port 49 and through the vapor passage 50 where it is pre-cooled.

Figure 5:
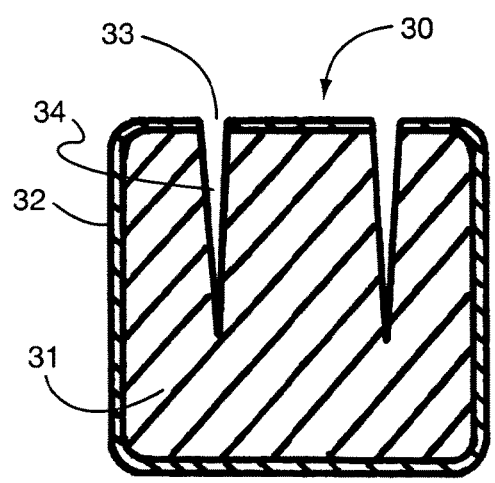
FIG. 5 is a sectional detail view of a tobacco cartridge, according to the preferred embodiment.

FIG. 5 depicts a sectional view of the tobacco cartridge 30. In the preferred embodiment, it consists of tobacco material 31, enclosed in a wrapper 32, with perforations 33, and aeration wells 34. The wrapped cartridge allows for the easy insertion and disposal of tobacco material without creating a mess, while the perforations allow the formed vapor to be released. When the cartridge is used up it can be easily disposed of in its entirety.

Here, tobacco or tobacco material is defined as any combination of natural and synthetic material that can be vaporized for pleasure or medicinal use. As an example, one test cartridge was prepared as embodiment of the present invention using flue-cured tobacco, glycerin, and flavorings. Those skilled in the art of tobacco product manufacture are familiar with these and other ingredients used for cigarettes, cigars, and the like. The test cartridge was produced by chopping tobacco into fine pieces (less than 3 mm diameter, preferably less than 2 mm), adding the other ingredients, and mixing until even consistency was achieved.

In the preferred embodiment, the cartridge is primarily cylindrical. In other embodiments, the form could be modified for various reasons. As an example, the walls of the cartridge might be drafted for easier insertion into the vaporization chamber. Or, the bottom of the cartridge might possess receptacles, which when combined with complimentary features on the surface cavity of the vaporization chamber would allow for more surface contact and hence improved thermal conduction.

Figure 6:
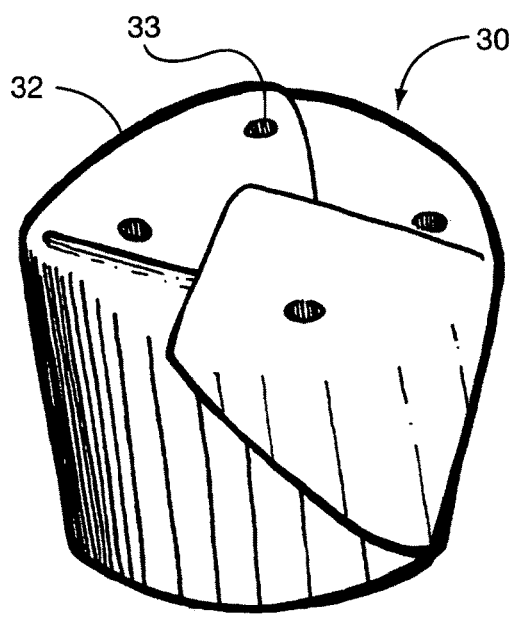
FIG. 6 is a perspective view of a tobacco cartridge, according to the preferred embodiment.

Any material could be used for the wrapper, provided that when heated to the operating temperature, it does not produce significant amounts of harmful gases. Aluminum foil and parchment paper are two examples. With papers, the cartridge would be manufactured in a folded-cup design, similar to that shown in FIG. 6. With films or metal foils, the wrapper could be pressed or blow-molded to the appropriate shape.

During manufacture of the preferred embodiment, the cartridge is enclosed on all sides, and perforated on the top so that vapors can emanate upwards. In the perforation step, or in an additional step, the optional aeration wells would be created.

Figure 7:
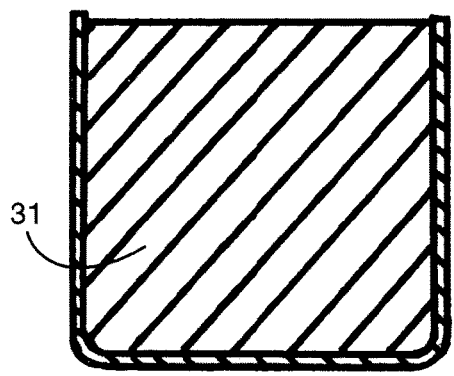
FIG. 7 is a sectional detail view of a tobacco cartridge, according to an alternate embodiment.

In an alternate embodiment, the cartridge might be wrapped on all sides but leaving the top exposed, as shown in FIG. 7. This is possible since the purpose of the wrapper is primarily to prevent tobacco material from touching the sides and bottom of the vaporization chamber.

In another embodiment, the material for the top of the cartridge might be vapor-permeable, such that perforations are not necessary.

In another embodiment, the cartridge as purchased by the user has no openings, but is punctured prior to insertion into the device, or upon introduction to the vaporization device. The latter could be achieved by adding a hollow puncturing means to the mouthpiece part of the device. For example, the inhalation passage of the mouthpiece could be extended by a hollow tube. When the mouthpiece is reinserted to close the device, it pierces the cartridge previously introduced, and allows a path for vapor to exit to the user.

Figure 8:
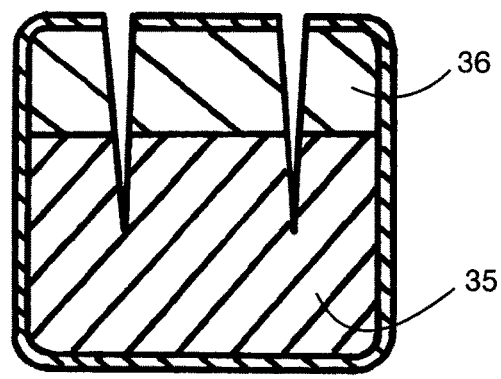
FIG. 8 is a sectional detail view of a tobacco cartridge, according to an alternate embodiment.

In the preferred embodiment, the tobacco material is a homogenous mixture. In another embodiment, there might be two layers, as shown in FIG. 8. The moist layer 35 has higher content of vapor-forming material than the dry layer 36, which consists of dry tobacco or other material acting as a filter. The dry layer serves to prevent any liquid from bubbling up and out of the cartridge during heating.

In another embodiment of the cartridge, a lower compartment might consist entirely of a vapor-forming medium, such as glycerine. An upper region would consist of the tobacco material to be vaporized, and the two would be separated by a material that only allows the medium to pass in a vapor or gaseous phase. Gore-tex (brand name) is one such material. In use, vapor generated in the lower region would pass through the semi-permeable membrane, volatize the active components of the tobacco, and a mix of the two would be delivered to the user upon inhalation.

In another embodiment, the consistency of the tobacco material is such that the wrapper is not necessary. This is possible if at least the outer surface of the cartridge is dry and cohesive enough to not leave deposits inside the device. Such a cartridge can be made by forming tobacco material in a mold. If the resulting surface is excessively moist, it can be dried by heating the cartridge in an oven.

It is to be understood that the present invention is not limited to the embodiments described above, but encompasses any and all embodiments within the scope of the following claims.

What is claimed is:

1. A device comprising:
   an electronic heater comprising a heat source and a vaporization chamber, the heat source disposed proximate to an exterior surface of the vaporization chamber, the vaporization chamber configured to hold a cartridge comprising a wrapper and a vaporizable material enclosed therein, the wrapper comprising a top surface and an opposing bottom surface, the exterior surface of the vaporization chamber configured to be disposed substantially parallel to the top surface of the wrapper when the cartridge is held within the vaporization chamber, wherein the heat source is positioned to heat the exterior surface of the vaporization chamber to generate an inhalable vapor from the vaporizable material;
   a controller, the controller configured to control an operating temperature of the vaporization chamber;
   a body, wherein the vaporization chamber and the heat source are disposed inside the body; and
   a mouthpiece in fluid communication with the vaporization chamber, the mouthpiece configured to deliver the inhalable vapor to a user, wherein the mouthpiece comprises an inhalation passage for releasing the inhalable vapor generated in the vaporization chamber to the user, wherein the mouthpiece is disposed at an end of the body, wherein the vaporization chamber is disposed proximate to the end of the body, wherein the inhalation passage extends towards the vaporization chamber, and wherein the mouthpiece comprises an inlet and an outlet, the inlet configured to allow passage of air into the vaporization chamber, the outlet configured to allow passage of the inhalable vapor out of the vaporization chamber to the user.

2. The device of claim 1, wherein the operating temperature of the device is at or below about 400 degrees Fahrenheit.

3. The device of claim 1, wherein the controller is further configured to maintain the operating temperature with a variation of less than about +/−5 degrees Fahrenheit.

4. The device of claim 1, further comprising one or more light-emitting diodes, the one or more light-emitting diodes configured to provide feedback on a state of at least one of the device or the cartridge.

5. The device of claim 4, wherein the feedback comprises at least one of:
   an indication that the device is on;
   an indication of a current temperature of the vaporization chamber;
   an indication that the current temperature of the vaporization chamber is below or has reached the operating temperature; or
   an indication that the inhalable vapor is ready for consumption.

6. The device of claim 1, wherein the vaporizable material comprises a combination of natural and synthetic material.

7. The device of claim 1, wherein the vaporizable material comprises a botanical.

8. The device of claim 1, wherein the vaporizable material comprises tobacco.

9. The device of claim 1, wherein the controller is further configured to receive a user selection corresponding to the operating temperature, the user selection selected from at least one of a plurality of discrete temperature settings or a range of operating temperature values.

10. The device of claim 1, further comprising an elongated main body having a first end and a second end, the second end opposite the first end along a longitudinal axis of the elongated main body, wherein the mouthpiece is disposed at the first end, wherein the vaporization chamber is disposed proximate to the first end.

11. The device of claim 1, further comprising the cartridge.

12. The device of claim 11, wherein the wrapper further comprises at least one side surface, the at least one side surface, the top surface and the opposing bottom surface configured to enclose the vaporizable material therein, at least one interior surface of the vaporization chamber configured to engage at least a portion of the at least one side surface when the cartridge is held within the vaporization chamber.

13. The device of claim 11, wherein the top surface of the wrapper comprises one or more perforations configured to enable upward flow of the inhalable vapor when the cartridge is held within the vaporization chamber.

14. The device of claim 11, wherein the wrapper is substantially cylindrical.

15. The device of claim 11, wherein the wrapper comprises a flexible material.

16. A device comprising:
an electronic heat source, the electronic heat source configured to operate at a prescribed operating temperature;
a vaporization chamber configured to hold a cartridge, the cartridge comprising a wrapper containing at least a vaporizable material, wherein the electronic heat source is disposed proximate to an exterior surface of the vaporization chamber, the exterior surface disposed substantially parallel to a bottom surface of the wrapper when the cartridge is held within the vaporization chamber, an interior surface of the vaporization chamber comprising one or more features configured to engage with one or more complementary features on a surface of the wrapper, the electronic heat source positioned to heat the exterior surface to generate an inhalable vapor from the vaporizable material; and
one or more light-emitting diodes configured to provide feedback on a state of at least one of the device or the cartridge;
wherein the one or more features of the interior surface of the vaporization chamber comprise one or more projections, and the one or more complementary features on a surface of wrapper comprise one or more receptacles.

17. The device of claim 16, further comprising a body, wherein the vaporization chamber and the heat source are disposed inside the body.

18. The device of claim 16, wherein the prescribed operating temperature of the device is at or below about 400 degrees Fahrenheit.

19. The device of claim 16, wherein a variation of a current temperature from the prescribed operating temperature is less than about +/−5 degrees Fahrenheit.

20. The device of claim 16, wherein the vaporizable material comprises a combination of natural and synthetic material.

21. The device of claim 16, wherein the vaporizable material comprises a botanical.

22. The device of claim 16, wherein the vaporizable material comprises tobacco.

23. The device of claim 16, further comprising an elongated main body extending in a longitudinal direction.

24. The device of claim 17, further comprising a mouthpiece in fluid communication with the vaporization chamber, the mouthpiece configured to deliver the inhalable vapor to a user;
wherein the mouthpiece comprises an inhalation passage for releasing the inhalable vapor generated in the vaporization chamber to a user, wherein the mouthpiece is disposed at an end of the body, wherein the vaporization chamber is disposed proximate to the end of the body, and wherein the inhalation passage is extended by a hollow tube into the vaporization chamber.

25. The device of claim 24, wherein the mouthpiece comprises an inlet and an outlet, the inlet configured to allow passage of air into the vaporization chamber, the outlet configured to allow passage of the inhalable vapor out of the vaporization chamber to the user.

26. The device of claim 16, wherein each of the one or more projections is configured to engage with one or of the one or more receptacles when the cartridge is held within the vaporization chamber.

27. The device of claim 16, wherein the one or more features of the interior surface of the vaporization chamber are configured to enable increased surface contact between the interior surface of the vaporization chamber and the surface of the wrapper after engagement with the one or more complementary features on the surface of the wrapper.

28. The device of claim 27, wherein the increased surface contact comprises a greater degree of surface contact after the engagement relative to a degree of surface contact between the interior surface of the vaporization chamber and the surface of the wrapper prior to the engagement.

29. The device of claim 16, wherein the one or more features of the interior surface of the vaporization chamber are configured to enable increased thermal conduction between the interior surface of the vaporization chamber and the surface of the wrapper after engagement with the one or more complementary features on the surface of the wrapper.

30. The device of claim 29, wherein the increased thermal conduction comprises a greater degree of thermal conduction after the engagement relative to a degree of thermal conduction between the interior surface of the vaporization chamber and the surface of the wrapper prior to the engagement.

31. The device of claim 16, wherein the feedback on the state of the at least one of the device or the cartridge comprises feedback indicative of the inhalable vapor being ready for consumption.

32. The device of claim 16, wherein the one or more complementary features on the surface of the wrapper are disposed on the bottom surface thereof.

* * * * *